(12) United States Patent
Chen

(10) Patent No.: US 7,918,222 B2
(45) Date of Patent: Apr. 5, 2011

(54) METHOD AND APPARATUS FOR TREATING OBSTRUCTIVE SLEEP APNEA BY USING NEGATIVE ORAL PRESSURE TO A PATIENT

(75) Inventor: Chung-Chu Chen, Hsinchu (TW)

(73) Assignee: Industrial Technology Research Institute, Hsinchu (TW)

( * ) Notice: Subject to any disclaimer, the term of this patent is extended or adjusted under 35 U.S.C. 154(b) by 780 days.

(21) Appl. No.: 11/727,696

(22) Filed: Mar. 28, 2007

(65) Prior Publication Data
US 2007/0277818 A1 Dec. 6, 2007

Related U.S. Application Data

(60) Provisional application No. 60/809,027, filed on May 30, 2006.

(51) Int. Cl.
*A61M 11/00* (2006.01)

(52) U.S. Cl. ......... 128/200.24; 128/207.14; 128/205.19; 128/207.15

(58) Field of Classification Search ............. 128/200.26, 128/201.26, 204.11, 204.18, 205.24, 206.29, 128/207.14, 207.15, 848, 861, 862, 205.19
See application file for complete search history.

(56) References Cited

U.S. PATENT DOCUMENTS

| 4,198,967 A * | 4/1980 | Dror | 128/860 |
| 5,465,734 A | 11/1995 | Alvarez et al. | |
| 5,957,133 A | 9/1999 | Hart | |
| 6,571,798 B1 * | 6/2003 | Thornton | 128/206.21 |
| 6,820,617 B2 * | 11/2004 | Robertson et al. | 128/204.18 |
| 2005/0166928 A1 | 8/2005 | Jiang | |
| 2006/0096600 A1 | 5/2006 | Witt et al. | |

FOREIGN PATENT DOCUMENTS

WO 2005074480 8/2005

OTHER PUBLICATIONS

Japanese Office Action dated Jan. 26, 2010.
Office communication in corresponding European patent application issued Jul. 6, 2010.

* cited by examiner

*Primary Examiner* — Steven O Douglas
(74) *Attorney, Agent, or Firm* — Bacon & Thomas, PLLC

(57) ABSTRACT

The present invention provides a method and apparatus for treating obstructive sleep apnea by using negative oral pressure to a patient. The present apparatus includes a vacuum unit for controlling and maintaining negative pressure of an oral cavity of the patient, a tube with one end thereof connecting to the vacuum unit to suck out air in the oral cavity to generate the negative pressure therein, and a mouthpiece connecting to the other end of the tube and fitting into and sealing the patient's mouth to prevent the oral cavity from air leakage. By using negative pressure in the oral cavity, the patient's soft palate is pulled toward the oral cavity and the patient's tongue is pulled toward an upper palate so as to maintain the patient's nasal air passageway open.

17 Claims, 5 Drawing Sheets

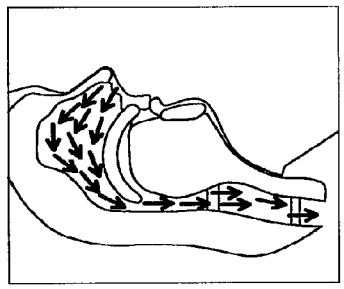
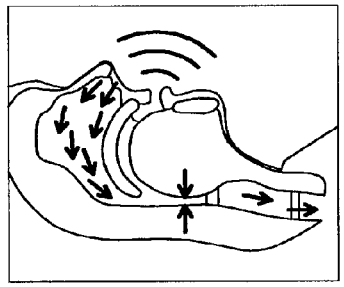
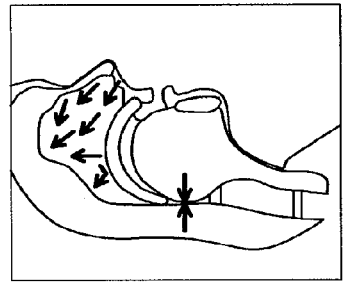
Fig. 1A (Prior Art)　　Fig. 1B (Prior Art)　　Fig. 1C (Prior Art)
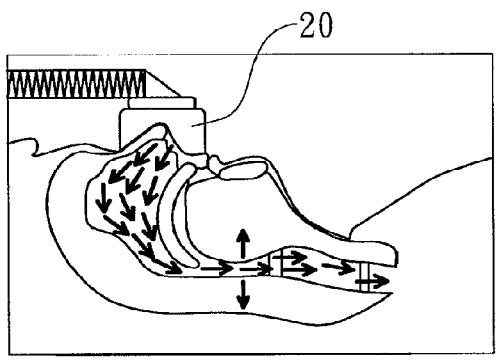
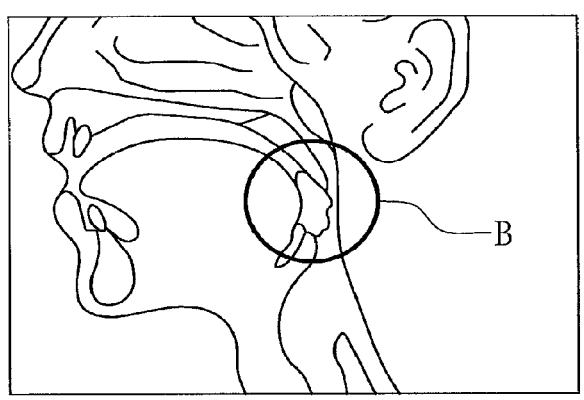
Fig. 2A (Prior Art)　　Fig. 2B (Prior Art)
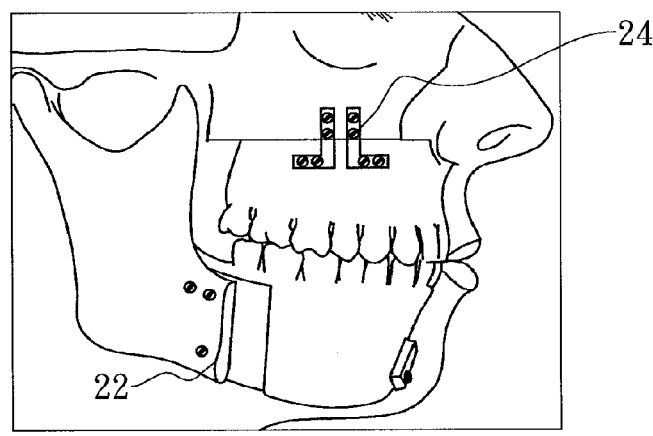
Fig. 2C (Prior Art)

METHOD AND APPARATUS FOR TREATING OBSTRUCTIVE SLEEP APNEA BY USING NEGATIVE ORAL PRESSURE TO A PATIENT

CROSS-REFERENCES TO RELATED APPLICATIONS

This application claims the benefit of the filing date of provisional application No. 60/809,027 filed May 30, 2006, under 35USC§119(e)(1).

BACKGROUND OF THE INVENTION

1. Field of the Invention

The present invention relates to a method and apparatus for treating obstructive sleep apnea by using negative oral pressure to a patient.

2. Description of the Related Art

Obstructive sleep apnea (OSA) occurs when the muscles in the back of people's throat relax in which people stop breathing sometimes hundreds of times a night for up to a minute each time. FIG. 1A depicts a normal breathing condition of people when sleeping in which the nasal breathing air passageway is kept open. FIG. 1B depicts an upper airway resistance syndrome of people when sleeping in which the dimension of the nasal breathing air passageway is narrowed due to relax of the back muscles of the throat. FIG. 1C depicts an obstructive sleep apnea occurs when sleeping in which the nasal breathing air passageway is obstructed by the collapsing muscles in the back of the throat.

More than 10% population is affected by sleep apnea but only a small fraction of patients are treated. People with sleep apnea have much higher life risks; for example having, excess mortality: there are 36% decrease in survival over 8 years in untreated patients with an apnea index of ≧20 as compared to untreated patient with an apnea index of <20, excess risk of hypertension: there is an odds ratio of 2:1 for a patient with Respiration Disorder Index (RDI)=5 as compared to a person without sleep apnea and an odds ratio of 5:1 for a patient with RDI=25 as compared to a person without sleep apnea, excess risk of myocardial infarction (MI): a patient with sleep apnea has 23-fold increased risk of recurrent MI, excess risk of stroke: an odds ratio of stroke is up to 3:2 for a patient with sleep apnea as compared to a person without sleep apnea, and risk of vehicular accidents: it is 7-fold higher for the untreated patient than a person without sleep apnea and 12-fold higher for the untreated patient if corrected for mileage.

There is no perfect resolution exists. The constant positive airway pressure (CPAP) method as shown in FIG. 2A is the most popular option, in which constant positive pressure air is supplied through a mask 20 to the patient to keep the nasal breathing air passageway open, but this option suffers a low patient compliance rate of 40~50% due to discomfort caused by positive pressure and high air flow. Other treatments include soft tissue removal, skeletal surgery and wearing an oral device. Referring to FIG. 2B, the soft tissue removal is to remove soft tissue such as soft palate, uvula and tonsil etc., as indicated in part B, to enlarge the dimension of the nasal breathing air passageway. FIG. 2C depicts a kind of skeletal surgery called bimaxillary advancement, by which a first fastener 22 is placed in the mandibular portion to push the mandibular portion forward and a second fastener 24 is placed in the upper palate such that the upper palate can be aligned with the mandibular portion. By pushing the mandibular portion forward, the tongue is pulled forward to enlarge the dimension of the nasal breathing air passageway. A comparison of different methods for treating obstructive sleep apnea is shown in Table I.

TABLE I

| Method | Cure for | Efficacy for treating OSA | Patient Compliance | Convenience | Cost (US$) | Insurance |
|---|---|---|---|---|---|---|
| Oral Device | Snore, Mild OSA | 20~40% | 50~60% | Not much | $$$ | Covered |
| CPAP | Snore, Mild-Severe | 75~85% | 20~50% | Not at all | $$$~$$$$ | Covered |
| Soft Tissue Removal | Snore, Mild OSA | <40% | 100% | Yes | $$$$ | Case by case |
| Skeletal Surgery | Moderate-Severe OSA | 40~97% | 100% | Yes, except Tracheostomy | $$$$$ | Case by case |

According to Table I, some of the above methods have high patient compliance but low efficacy and also high prices, some of them have high efficacy, low prices but also low patient compliance as well as low convenience.

It is desirable to provide a method and an apparatus for treating OSA, which can alleviate the drawbacks of the above methods.

SUMMARY OF THE INVENTION

A primary objective of this invention is to provide a method and apparatus that have high efficacy and high compliance to cure the obstructive sleep apnea.

For achieving the above objective, the present invention provides a method for treating snoring or sleep apnea, which uses negative pressure in an oral cavity of a user to pull the user's soft palate toward the oral cavity and the user's tongue toward an upper palate so as to maintain the user's nasal air passageway open.

In one another aspect, the present invention provides an apparatus for treating obstructive sleep apnea by using negative oral pressure to a patient, which comprises a vacuum unit for controlling and maintaining negative pressure of an oral cavity of the patient, a tube with one end thereof connecting to the vacuum unit to suck out air in the oral cavity to generate the negative pressure therein, and a mouthpiece connecting to the other end of the tube and fitting into and sealing the patient's mouth to prevent the oral cavity from air leakage.

The present apparatus has a simple structure that is easily made, and also providing high efficacy to cure the obstructive sleep apnea and high compliance to the patient. The present apparatus has a huge commercial potential.

BRIEF DESCRIPTION OF THE DRAWINGS

FIG. 1A is a schematic view depicting a normal breathing condition of people when sleeping FIG. 1B is a schematic view depicting an upper airway resistance syndrome of people when sleeping;

FIG. 1C is a schematic view depicting obstructive sleep apnea occurs when sleeping;

FIG. 2A depicts using a constant positive airway pressure (CPAP) device to treat the obstructive sleep apnea;

FIG. 2B depicts a sectional view of a human's face;

FIG. 2C depicts using skeletal surgery to treat the obstructive sleep apnea;

DETAILED DESCRIPTION OF THE PREFERRED EMBODIMENTS

Figure 3A:
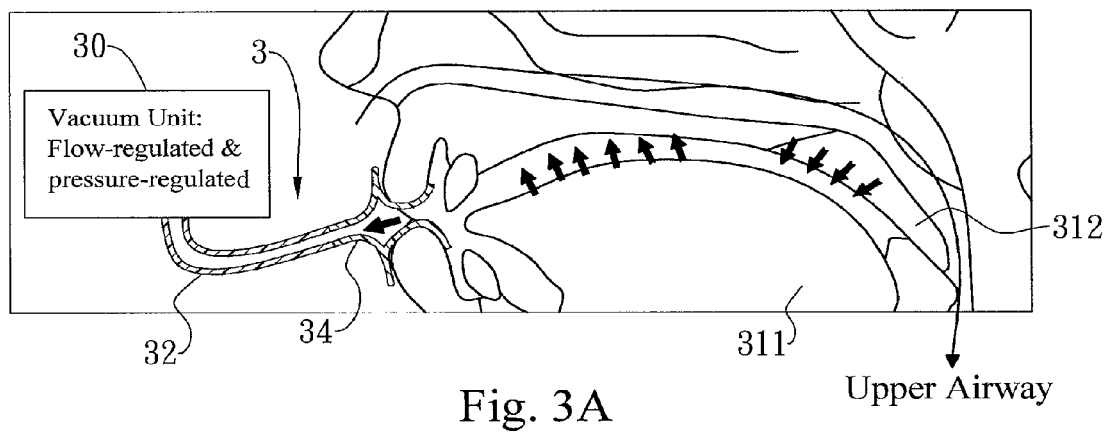
FIG. 3A is a schematic view of the present apparatus according to a first embodiment of this invention.

The present invention provides an apparatus for treating obstructive sleep apnea by using negative oral pressure to a patient. FIG. 3A is a schematic view of the present apparatus according to a first embodiment of this invention. In the first embodiment, the present apparatus for treating obstructive sleep apnea 3 includes: a vacuum unit 30 for controlling and maintaining negative pressure of an oral cavity of the patient; a tube 32 with one end thereof connecting to the vacuum unit 30 to suck out air in the oral cavity to generate the negative pressure therein; and a mouthpiece 34 connecting to the other end of the tube 32 and fitting into and sealing the patient's mouth to prevent the oral cavity from air leakage.

The present invention uses the vacuum unit 30 via the tube 32 and the mouthpiece 34 to suck out air in the oral cavity of the patient such that negative pressure can be maintained in the oral cavity. The pressure difference between the nasal cavity and oral cavity pushes the soft palate 312 toward the oral cavity, and the vacuum also pulls the tongue 311 toward the upper palate. As such, an upper airway (i.e. the nasal breathing air passageway) can be opened to prevent the patient from the obstructive sleep apnea (OSA). The mouthpiece 34 is an interface of the oral cavity and vacuum unit 30. The mouthpiece 34 fits in the patient's mouth and seals the mouth to prevent from losing vacuum in the oral cavity. The vacuum unit 30 can be a pressure-regulated and/or flow-regulated vacuum pump to maintain negative pressure in the oral cavity overtime. A manual pump can also be used to as the vacuum unit 30.

Figure 3B:
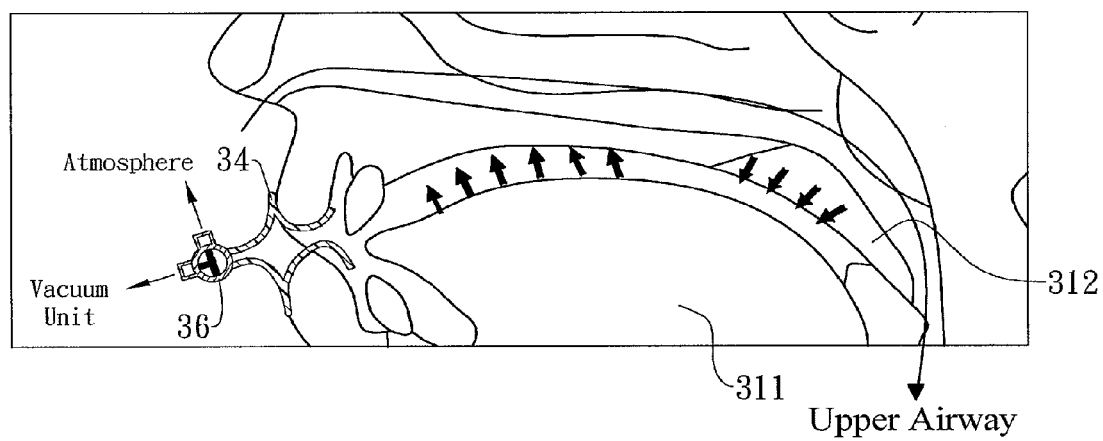
FIG. 3B is a schematic view of the present apparatus according to a second embodiment.

FIG. 3B is a schematic view of the present apparatus according to a second embodiment. In the second embodiment, a switching valve 36 is associated with the mouthpiece 34, while the remainder of the apparatus is the same with the first embodiment. The switching valve 36 can connect the oral cavity to the tube 32 and vacuum unit 30 in operation. The switching valve 36 can close the oral cavity to maintain the negative pressure of the oral cavity while the tube 32 and the vacuum unit 30 can be disconnected with the mouthpiece 34. The switching valve 36 can also connect the oral cavity to the atmosphere for devaccuming and recovering of normal pressure in the oral cavity.

Figure 3C:
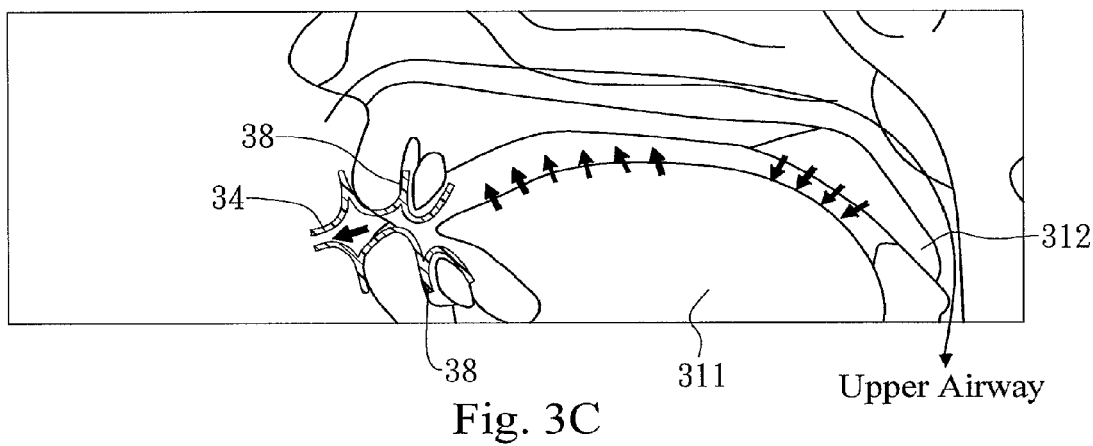
FIG. 3C is a schematic view of the present apparatus according to a third embodiment.

FIG. 3C is a schematic view of the present apparatus according to a third embodiment of this invention. In the third embodiment, a teeth engaging part 38 is cooperated with the mouth piece 34 to hold the patient's mandibular position such that further improving the openness of the upper airway. The remainder of the apparatus of the third embodiment is the same with the first embodiment. Alternatively, the teeth engaging part 38 and the valve 36 also can be used together in the present apparatus (not shown).

Figure 3D:
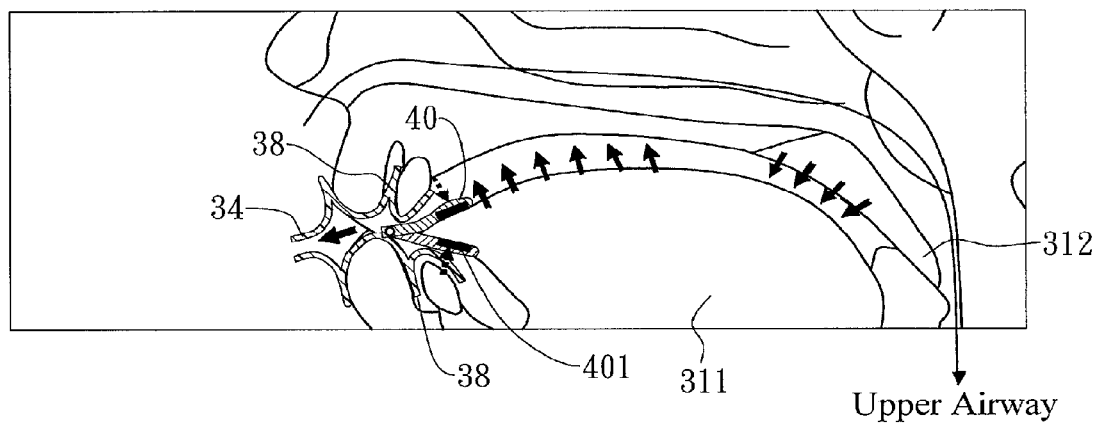
FIGS. 3D and 3E are schematic views of the present apparatus according to a fourth embodiment.
Figure 3E:
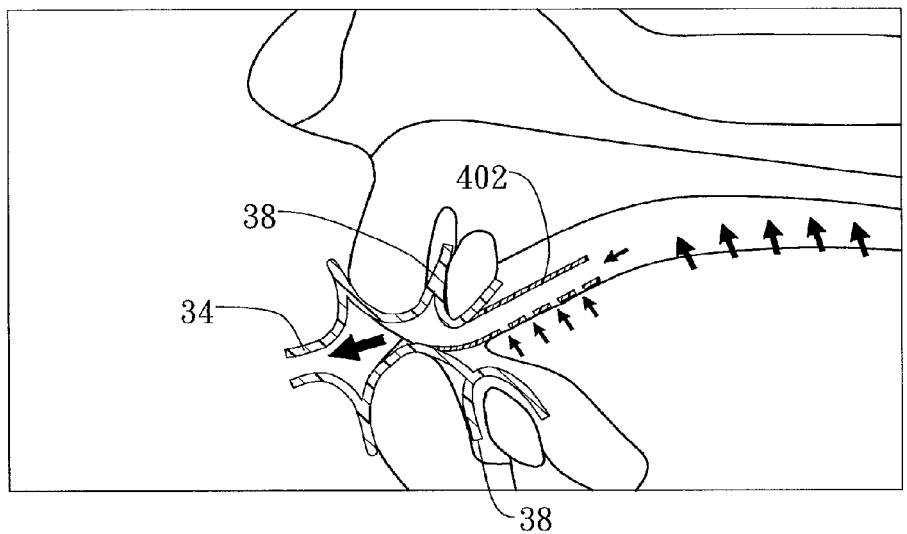

FIGS. 3D and 3E are schematic views of the present apparatus according to a fourth embodiment of this invention. In the fourth embodiment, a tongue retaining part 40 is fastened at one end of the mouthpiece 34 opposite to the tube 32 to hold the tongue from being falling back in supine sleep position. The use of the tongue retaining part 40 also improves the openness of the upper airway. The tongue retaining part 40 can be provided with a pair of magnetic plates 401 opposite to each other to hold the tongue by magnetic force, or formed of a spring-loaded clamp. See FIG. 3E, the tongue retaining part 40 also can be instead of a vacuum conduit 402 to hold the tongue by vacuum force.

Figure 3F:
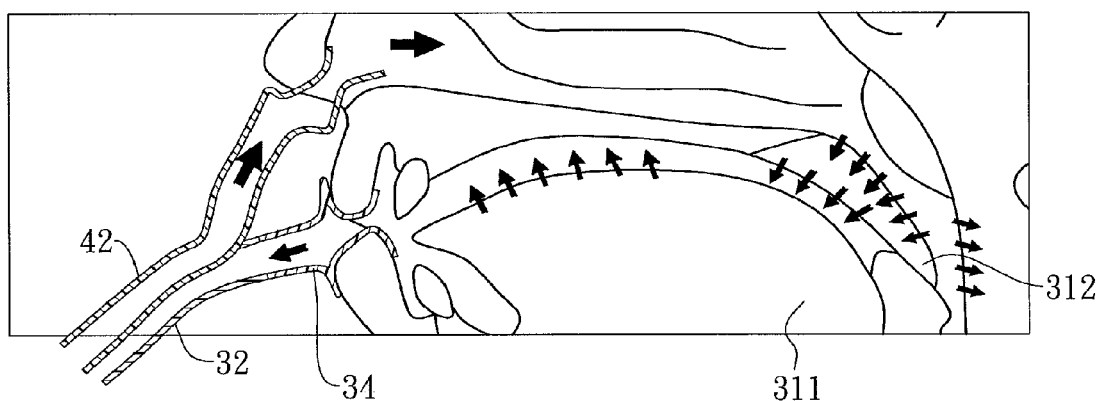
FIG. 3F is a schematic view of the present apparatus according to a fifth embodiment.

FIG. 3F is a schematic view of the present apparatus according to a fifth embodiment of this invention. In the fifth embodiment, a positive nasal pressure and the negative oral pressure are combined together to maintain the openness of the upper airway. A nasal tube 42 connecting with a constant positive airway pressure (CPAP) device (not shown) is associated with the tube 32. The nasal tube 42 and the tube 32 can be integrally formed. The positive air pressure is supplied in the nasal cavity by the constant positive airway pressure device through the nasal tube 42. In the fifth embodiment, the positive pressure in the nasal cavity and the negative pressure in the oral cavity are combined together such that the constant positive airway pressure device does not need to provide high air pressure and high air flow into the nasal cavity. The discomfort caused by the high air pressure and high air flow in the upper airway is eliminated and the patient compliance to this apparatus is improved. In other words, this apparatus and its method can reduce the pressure setting needed for the traditional constant pressure airway device for treating obstructive sleep apnea. Therefore, it can reduce the discomfort caused by high pressure and high air flow.

Figure 3G:
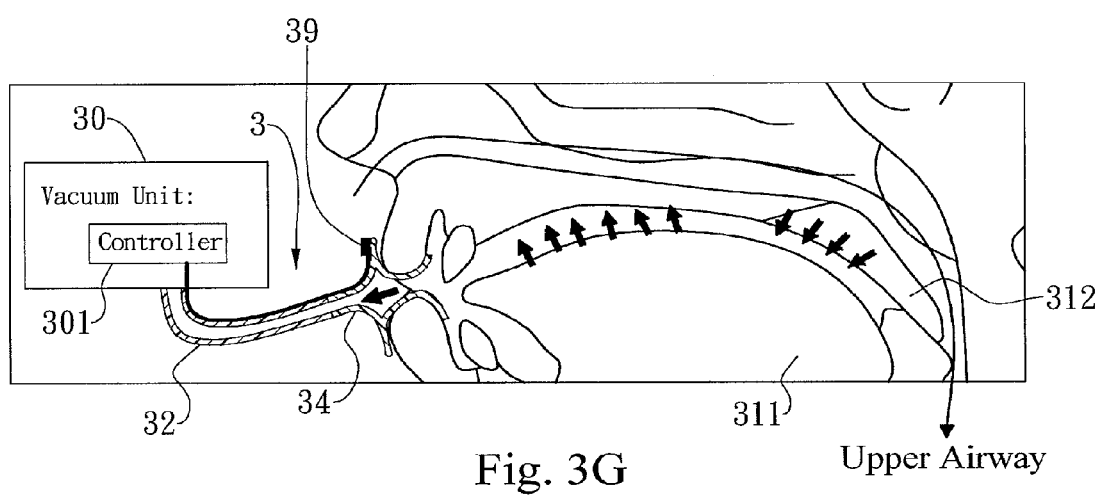
FIG. 3G is a schematic view of the present apparatus according to a sixth embodiment.

FIG. 3G is a schematic view of the present apparatus according to a sixth embodiment. In the sixth embodiment, a flow sensor 39 is associated with the mouthpiece 34, while the remainder of the apparatus is the same with the first embodiment. The flow sensor 39 is used to sense the nasal flow pattern. For example, the flow sensor 39 may detect temperature change or pressure variation, as upper airway flow is varied during normal and disordered breathing. The signal from the flow sensor 39 is fed back to a controller 301 inside the vacuum unit 30. The controller 301 may start, stop or adjust the pressure and flow setting of the vacuum unit 30 based on the sensed upper airway flow pattern.

While the invention has been described by way of examples and in terms of preferred embodiments, it is to be understood that those who are familiar with the subject art can carry out various modifications and similar arrangements and procedures described in the present invention and also achieve the effectiveness of the present invention. Hence, it is to be understood that the description of the present invention should be accorded with the broadest interpretation to those who are familiar with the subject art, and the invention is not limited thereto.

What is claimed is:

1. An apparatus for treating obstructive sleep apnea by using negative oral pressure to a patient, comprising:
   a vacuum unit for controlling and maintaining negative pressure of an oral cavity of the patient;
   a tube with one end thereof connecting to said vacuum unit to suck out air in the oral cavity to generate the negative pressure therein; and
   a mouthpiece connecting to the other end of said tube and having at least one concave portion conforming to a contour of at least one of an upper lip and a lower lip of the patient for attaching to at least one of the upper lip and the lower lip and sealing said patient's mouth to prevent the oral cavity from air leakage.

2. The apparatus of claim 1, wherein said vacuum unit is an automatic pump or a manual pump.

3. The apparatus of claim 1, further comprising a switching valve associated with said mouthpiece, wherein said switching valve connects the oral cavity to said tube and said vacuum unit in operation, said switching valve closes the oral cavity to maintain the negative pressure of the oral cavity while said tube and said vacuum unit can be disconnected with said mouthpiece, or said switching valve connects the oral cavity to the atmosphere for recovery of normal pressure in the oral cavity.

4. The apparatus of claim 1, further comprising a teeth engaging part cooperated with said mouth piece to hold the patient's mandibular position.

5. The apparatus of claim 3, further comprising a teeth engaging part cooperated with said mouth piece to hold the patient's mandibular position.

6. The apparatus of claim 1, further comprising a tongue retaining part fastened at one end of said mouth piece opposite to said tube to hold the patient's tongue position.

7. The apparatus of claim 3, further comprising a tongue retaining part fastened at one end of said mouth piece opposite to said tube to hold the patient's tongue position.

8. The apparatus of claim 4, further comprising a tongue retaining part fastened at one end of said mouth piece opposite to said tube to hold the patient's tongue position.

9. The apparatus of claim 6, wherein said tongue retaining part uses vacuum force, magnetic force or spring-loaded force to hold the patient's tongue position.

10. The apparatus of claim 7, wherein said tongue retaining part uses vacuum force, magnetic force or spring-loaded force to hold the patient's tongue position.

11. The apparatus of claim 8, wherein said tongue retaining part uses vacuum force, magnetic force or spring-loaded force to hold the patient's tongue position.

12. The apparatus of claim 1, further comprising a nasal tube associated with said tube, said nasal tube connecting to a constant positive airway pressure (CPAP) device.

13. The apparatus of claim 12, wherein said nasal tube and said tube are integrally formed.

14. The apparatus of claim 4, further comprising a nasal tube associated with said tube, said nasal tube connecting to a constant positive airway pressure (CPAP) device.

15. The apparatus of claim 6, further comprising a nasal tube associated with said tube, said nasal tube connecting to a constant positive airway pressure (CPAP) device.

16. The apparatus of claim 1, further comprising a flow sensor associated with said mouthpiece for sensing nasal flow patterns, said flow sensor connecting to a controller inside said vacuum unit.

17. A method for treating snoring or sleep apnea using the apparatus of claim 1, comprising:
   applying negative pressure to an oral cavity of a user to pull the user's soft palate toward the oral cavity and the user's tongue toward an upper palate so as to maintain the user's nasal air passageway open.

* * * * *